(12) United States Patent
Lau

(10) Patent No.: US 10,149,700 B2
(45) Date of Patent: Dec. 11, 2018

(54) 3 DIMENSIONAL SIMULTANEOUS MULTIPLE CORE BIOPSY OR FIDUCIAL MARKER PLACEMENT DEVICE AND METHODS

(71) Applicant: Jan R. Lau, Windsor, CA (US)

(72) Inventor: Jan R. Lau, Windsor, CA (US)

(73) Assignees: Jan R. Lau, Windsor, CA (US); David Liu, Point Roberts, WA (US)

( * ) Notice: Subject to any disclaimer, the term of this patent is extended or adjusted under 35 U.S.C. 154(b) by 649 days.

(21) Appl. No.: 14/455,750

(22) Filed: Aug. 8, 2014

(65) Prior Publication Data

US 2015/0045665 A1 Feb. 12, 2015

Related U.S. Application Data

(60) Provisional application No. 61/865,063, filed on Aug. 12, 2013, provisional application No. 61/899,029, filed on Nov. 1, 2013.

(51) Int. Cl.
*A61B 6/00* (2006.01)
*A61B 17/34* (2006.01)
(Continued)

(52) U.S. Cl.
CPC ...... *A61B 17/3468* (2013.01); *A61B 10/0275* (2013.01); *A61B 10/04* (2013.01); *A61B 90/39* (2016.02); *A61M 25/0084* (2013.01); *A61B 2010/0208* (2013.01); *A61B 2017/00867* (2013.01); *A61B 2090/392* (2016.02); *A61B 2090/3966* (2016.02); *A61B 2090/3987* (2016.02); *A61M 2025/0086* (2013.01)

(58) Field of Classification Search
None
See application file for complete search history.

(56) References Cited

U.S. PATENT DOCUMENTS

| 5,415,182 A | 5/1995 | Chin et al. |
| 6,425,887 B1 | 7/2002 | McGuckin et al. |
| (Continued) | | |

FOREIGN PATENT DOCUMENTS

| EP | 1767167 | 3/2007 |
| EP | 1767167 A2 | 3/2007 |
| WO | WO2011/004776 | 1/2011 |

OTHER PUBLICATIONS

International Search Report and Written Opinion dated Dec. 5, 2014 for PCT/US2014/050592.

*Primary Examiner* — Amelie R Gillman
(74) *Attorney, Agent, or Firm* — Stoel Rives LLP

(57) ABSTRACT

Systems and methods for non-serial, substantially simultaneous or simultaneous tissue sampling and placement of multiple markers/fiducials in a non-linear, distributed or three dimensional configuration. The systems and methods can be applicable to other forms and combinations of distributed/3 dimensional/spherical localization which may include a single procedure or combination of procedures that may include 3D biopsy, fiducial placement, brachytherapy seed placement, injection/infusion of bioactive materials (e.g., chemotherapy, small molecules, cellular materials, cells, caustic materials, proteolytics, embolic material, glue, etc.), thermally or electrically derived ablation.

13 Claims, 12 Drawing Sheets

(51) Int. Cl.
*A61B 10/04* (2006.01)
*A61M 25/00* (2006.01)
*A61B 10/02* (2006.01)
*A61B 17/00* (2006.01)
*A61B 90/00* (2016.01)

(56) References Cited

U.S. PATENT DOCUMENTS

| | | | |
|---|---|---|---|
| 6,575,991 B1 * | 6/2003 | Chesbrough | A61B 17/3468 606/185 |
| 7,465,279 B2 | 12/2008 | Beckman et al. | |
| 7,473,232 B2 | 1/2009 | Teague | |
| 7,517,348 B2 | 4/2009 | Vetter et al. | |
| 7,828,746 B2 | 11/2010 | Teague | |
| 7,846,107 B2 | 12/2010 | Hoffman et al. | |
| 8,052,661 B2 | 11/2011 | McGuckin, Jr. et al. | |
| 2001/0047169 A1 | 11/2001 | McGuckin et al. | |
| 2002/0026188 A1 * | 2/2002 | Balbierz | A61B 18/1206 606/41 |
| 2005/0075580 A1 * | 4/2005 | Leigh | A61B 10/0266 600/567 |
| 2005/0148866 A1 * | 7/2005 | Gunderson | A61M 25/0012 600/431 |
| 2006/0184090 A1 * | 8/2006 | Davis | A61M 31/007 604/19 |
| 2009/0088665 A1 | 4/2009 | Beckman et al. | |
| 2009/0187118 A1 | 7/2009 | Kim et al. | |
| 2009/0216150 A1 * | 8/2009 | Reichel | A61B 90/39 600/562 |
| 2012/0022314 A1 * | 1/2012 | Sing | A61B 90/39 600/3 |
| 2012/0123427 A1 | 5/2012 | McGuckin, Jr. et al. | |
| 2012/0302935 A1 * | 11/2012 | Miller | A61B 17/32072 604/8 |
| 2012/0330185 A1 | 12/2012 | Coonahan et al. | |
| 2013/0041256 A1 | 2/2013 | Fiebig et al. | |

* cited by examiner

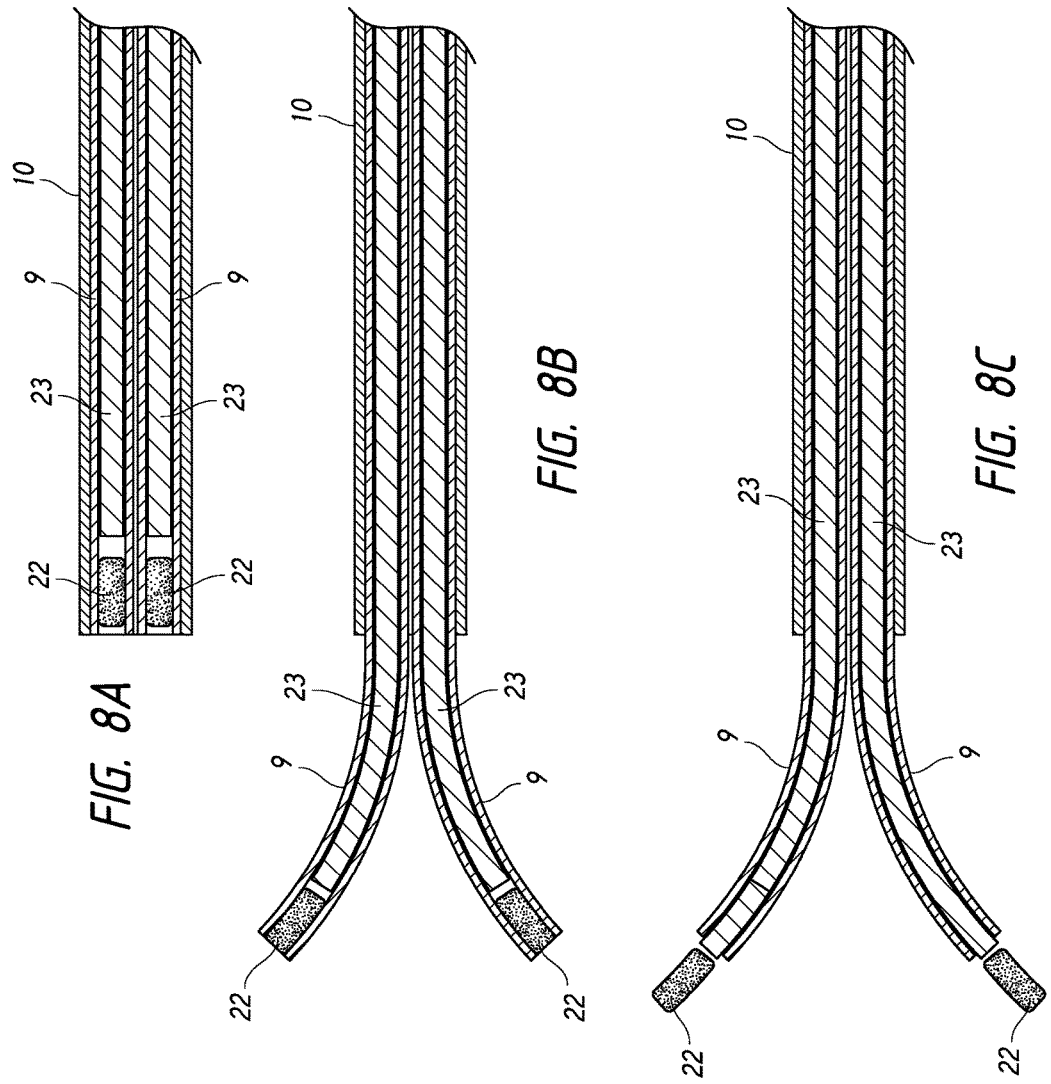

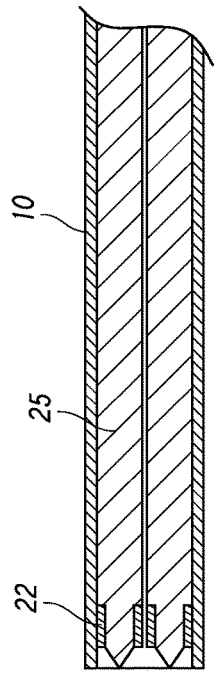
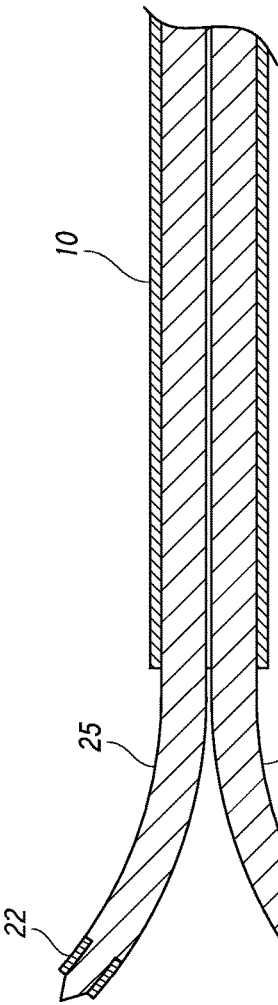
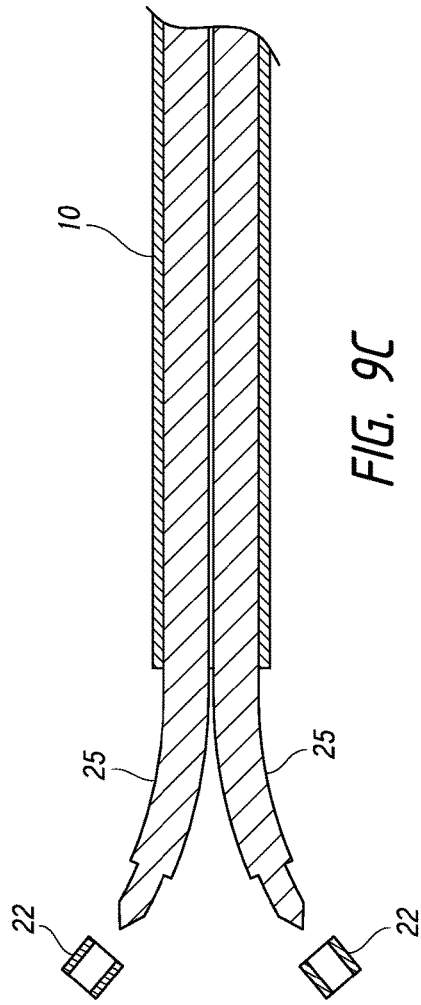
FIG. 9A
FIG. 9B
FIG. 9C

3 DIMENSIONAL SIMULTANEOUS MULTIPLE CORE BIOPSY OR FIDUCIAL MARKER PLACEMENT DEVICE AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference in their entireties and made a part of the present disclosure.

BACKGROUND

Field

The disclosure relates to a method in which multiple geographically distributed solid core biopsies can be obtained simultaneously alongside with simultaneous fiducial marker placement. The disclosure also relates to similar methods along with the systems and techniques for accomplishing the preferred methods in addition to disclosure of additional applications.

Description of Related Art

Systemic and locally directed therapy targeting specific organs or tissue often requires a tissue sample to be performed through localization by physical examination, intraoperative visualization or image guided procedures in order to diagnose disease (e.g., cancer, organ failure, infection, etc.) and predict or prognosticate what type of therapy should ensue. Oftentimes within the targeted tissue, variability and inhomogeneity exists thus potentially limiting the utility of a single pass sample or biopsy that is performed in a linear fashion. As a result, multiple passes and multiple localizations of the targeted tissue must be conducted in order to provide adequate representation of the variability of the targeted tissue, which is either unachievable with current linear biopsy methods or may require multiple localizations of the tissue resulting in increased risk, decreased reliability and inadequate sampling.

In addition, during the course of biopsy, confirmation of the region of biopsy is required to confirm the region of sample, and anticipate further therapy such as external radiation beam therapy, or surgery. However current manifestations of marker placement and localization require a completely separate procedure, with separate methods and devices which may result in increased complication rates, prolonged patient discomfort and prolonged operating time.

A number of patents in the prior art describe acquisition of multiple core biopsy samples obtained in a linear fashion resulting in repeated sampling of a targeted region without the ability to further steer/direct or sample other geographic regions without manipulating the entire device or repeating the procedure. Other devices describe extracting tissue samples in a non-linear fashion through the maceration and homogenization of tissue, thus destroying tissue architecture which may be essential for proper diagnosis and also result in seeding of potential tumor cells outside of the original location of interest.

SUMMARY

The systems, methods and devices described herein have innovative aspects, no single one of which is indispensable or solely responsible for their desirable attributes. Without limiting the scope of the claims, some of the advantageous features will now be summarized.

An embodiment involves a method of accessing multiple locations within an organ or tissue, comprising: positioning an introducer at a desired location within the organ or tissue; removing a stylet from the introducer; coupling an access device to the introducer; adjusting the access device to a selected deployment distance; simultaneously or substantially simultaneously deploying multiple tines the deployment distance such that end portions of each of the multiple tines are distributed at spaced locations from one another; using the multiple tines to do one or more of: obtain tissue samples, deploy markers or deliver a therapeutic.

In some configurations, the using the multiple tines comprises doing two or more of: obtaining tissue samples, deploying markers or delivering therapeutics with one or more of the multiple tines. In some configurations, the deployment distance of each of the multiple tines is identical or substantially identical. In some configurations, the deployment distance of each of the multiple tines is a radial distance from a longitudinal axis of the introducer.

An embodiment involves a method of accessing multiple locations within an organ or tissue, comprising: positioning an introducer conduit at a desired location within the organ or tissue; simultaneously or substantially simultaneously deploying multiple tines through the introducer conduit to a deployment distance such that end portions of each of the multiple tines are distributed at spaced locations from one another; using the multiple tines to do one or more of: obtain tissue samples, deploy markers or deliver a therapeutic.

In some configurations, the using the multiple tines comprises doing two or more of: obtaining tissue samples, deploying markers or delivering therapeutics with one or more of the multiple tines. In some configurations, the deployment distance of each of the multiple tines is identical or substantially identical. In some configurations, the deployment distance of each of the multiple tines is a radial distance from a longitudinal axis of the introducer.

An embodiment involves a method of simultaneously or substantially simultaneously obtaining a tissue sample and placing a fiducial marker, comprising: deploying an inner member of a coaxial tine assembly to a desired location, the inner member comprising a sample collection space and carrying a fiducial marker; deploying an outer member of the coaxial tine assembly over the inner member to obtain a tissue sample when the outer member passes over the sample collection space; withdrawing the coaxial tine assembly from the desired location and leaving the fiducial marker in the desired location.

In some configurations, the deploying of the outer member comprises separating the fiducial marker from the inner member when the fiducial marker is contacted by the outer member.

An embodiment involves a method of simultaneously or substantially simultaneously obtaining a tissue sample and placing a fiducial marker at multiple locations within an organ or tissue, comprising: positioning an introducer assembly at a desired location within the organ or tissue, the introducer assembly comprising a conduit and a stylet; removing the stylet from the introducer assembly; coupling biopsy device to the introducer; retracting a sliding member of the biopsy device against a biasing force of a biasing member, wherein the sliding member carries an outer portion of each of a plurality of coaxial tine assemblies; adjusting the biopsy device to a selected deployment distance by adjusting an axial position of the biopsy device relative to the conduit; simultaneously or substantially simultaneously deploying an inner portion of each of the coaxial tine assemblies the deployment distance such that end portions of each of the inner portions of the coaxial tine assemblies are distributed at spaced locations from one another; releasing the sliding member such that the biasing member moves the sliding member to deploy the outer portions of the coaxial tine assemblies to obtain tissue samples and deploy the fiducial markers.

In some configurations, the deploying of the inner portions of the coaxial tine assemblies is accomplished by the pressing of a trigger of the biopsy device. In some configurations, the releasing of the sliding member is accomplished by the pressing of the trigger of the biopsy device. In some configurations, the releasing of the sliding member occurs after the inner portions have been deployed substantially to the deployment distance.

An embodiment involves a combination biopsy and marker placement device, comprising: a first portion comprising an introducer conduit and a stylet; a second portion that is securable to the first portion at a selected relative position within a range of available positions, the second portion comprising: a body; a slider movable along a longitudinal axis of the device; a biasing element that biases the slider in a deployment direction; a trigger movable along the longitudinal axis of the device; a plurality of coaxial tine assemblies, wherein a first portion of each of the tine assemblies are coupled for movement with the trigger and a second portion of each of the tine assemblies are coupled for movement with the slider, wherein each tine assembly carries a marker; wherein, in use, the introducer conduit is positioned at a desired location within an organ or tissue and the stylet is removed from the introducer conduit, the second portion is coupled to the first portion at the selected position, the slider is retracted against the force of the biasing element, the trigger is depressed to simultaneously or substantially simultaneously deploy the first portions of the tine assemblies and the slider is released to deploy the second portions of the tine assemblies, wherein the tissue samples are taken when the second portions of the tine assemblies are deployed over the first portions, and wherein when the tine assemblies are removed the markers are left in place.

In some configurations, the trigger is configured to release the slider once the first portions of the tine assemblies are substantially deployed. In some configurations, the first portions of the tine assemblies carry the markers and the markers are separated from the first portions by the movement of the second portions over the first portions. In some configurations, distal end portions of the tine assemblies have a curved shape and are restrained in a generally linear orientation by the introducer conduit. In some configurations, an adjustment mechanism permits adjustment of the second portion relative to the first portion to adjust a deployment distance of the tine assemblies. In some configurations, a retention mechanism retains the slider in a retracted position until released.

An embodiment involves a combination biopsy, marker placement or therapeutic delivery device, comprising: a first portion comprising an introducer conduit; a second portion that is securable to the first portion at a selected relative position within a range of available positions, the second portion comprising a plurality of coaxial tine assemblies, wherein a first portion of each of the tine assemblies are movable relative to a second portion of each of the tine assemblies, wherein end portions of the tine assemblies have a curved shape and can be restrained in a generally linear configuration by the introducer conduit; wherein the introducer conduit can be positioned at a desired location within an organ or tissue, the first portions of the tine assemblies can be deployed such that the end portions are at spaced locations from one another due to the curved shape, the second portions of the tine assemblies can be deployed, and the tine assemblies can be removed such that each tine assembly performs one or more of: obtaining a tissue sample, deploying a marker and delivering a therapeutic substance.

BRIEF DESCRIPTION OF THE DRAWINGS

These and other features, aspects and advantages of the present biopsy devices and methods are described in greater detail below with reference to drawings of several preferred embodiments, which are intended to illustrate but not to limit the present invention. The drawings contain twelve (12) figures.

FIGS. 8A-8C are enlarged, cross-sectional view of fiducial marker implantation using one embodiment of the device.

FIGS. 9A-9C are enlarged, cross-sectional view of fiducial marker implantation using another embodiment of the device.

DETAILED DESCRIPTION

Figure 1:
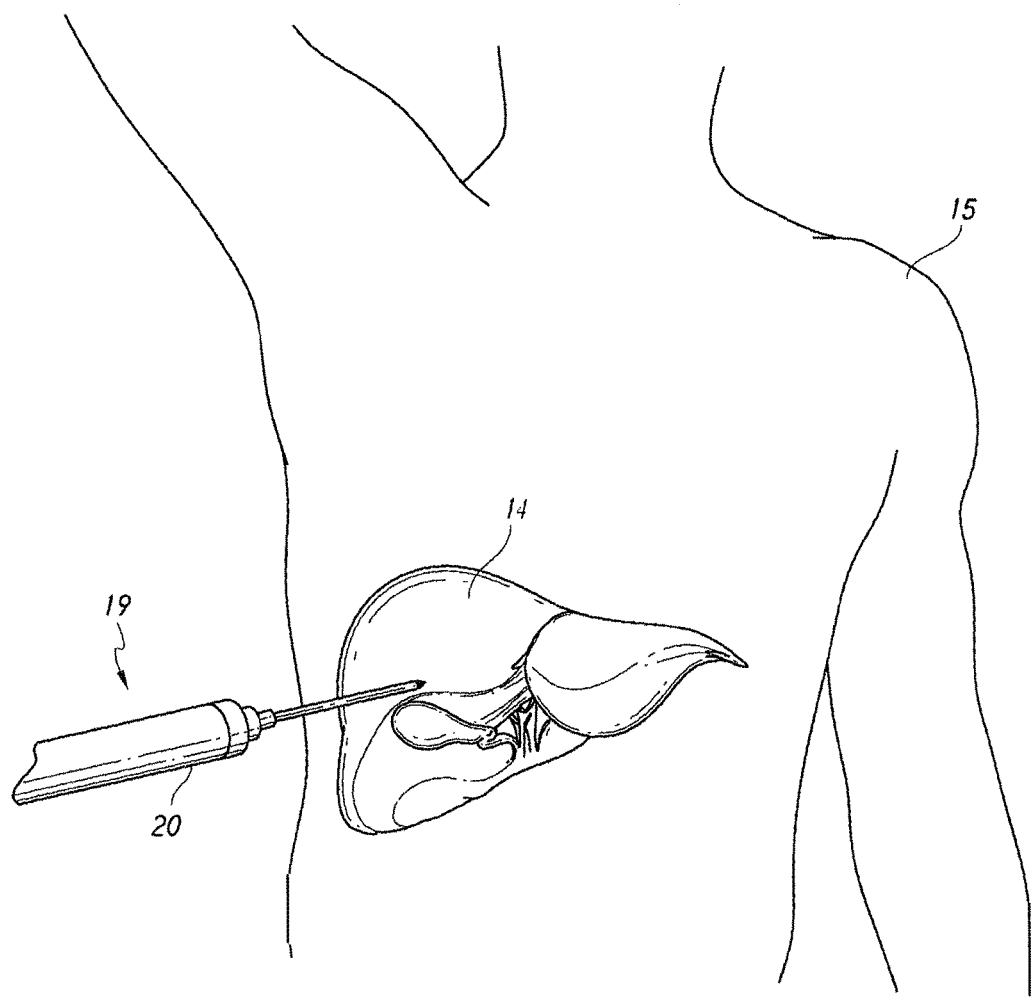
FIG. 1 is an illustration of a system and device having certain features, aspects and advantages of a preferred embodiment used to conduct a liver biopsy procedure.
Figure 2:
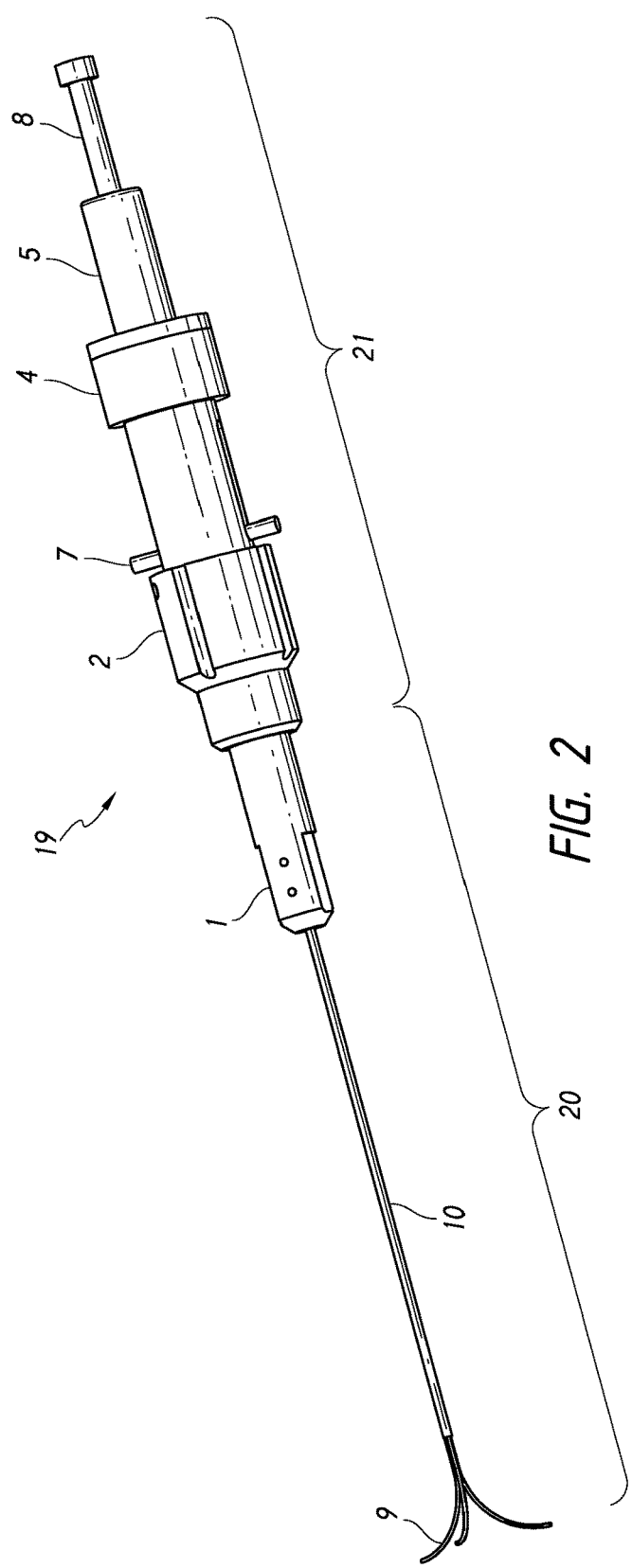
FIG. 2 is a perspective view of an introducer and biopsy needle mated together.
Figure 3:
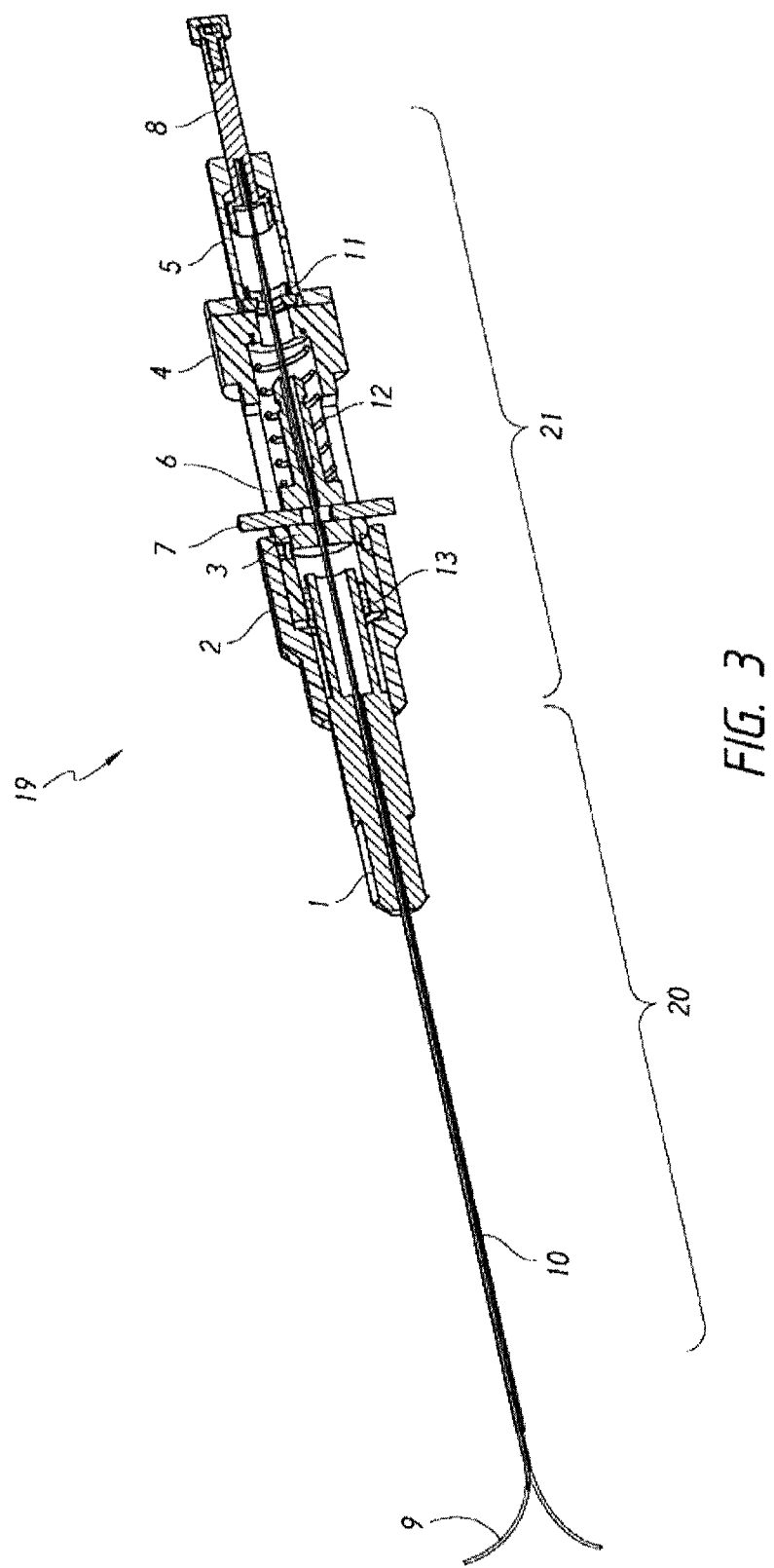
FIG. 3 is a cross-sectional view along the longitudinal axis of the introducer and biopsy needle.

The ability to document the specific regions of sample for further planning for treatment utilizing a tissue marker or fiducial marker has remained a cumbersome process when examining the prior art capable of only placing a single marker, or multiple markers placed in a straight line which may result in difficulty localizing the area of targeted therapy (such as for forms of external radiation therapy [e.g., stereotactic beam radiotherapy, proton beam therapy, cyberknife]). Embodiments of the current invention allow for non-serial, substantially simultaneous or simultaneous placement of multiple markers/fiducials in a non-linear, distributed or three dimensional configuration for the purposes of improved localization of aforementioned targeted tissue.

Furthermore, the methods described may also be applicable to other forms and combinations of distributed/3 dimensional/spherical localization which may include a single procedure or combination of procedures that may include 3D or volumetric biopsy (core or aspiration), fiducial placement, brachytherapy seed placement, injection/infusion of bioactive materials (e.g., chemotherapy, small molecules, cellular materials, cells, caustic materials, proteolytics, embolic material, glue, etc.), thermally or electrically derived ablation (radiofrequency ablation, microwave ablation, cryoablation, irreversible electroporation). For convenience, any recitation of distributed, volumetric, 3 dimensional or spherical herein can also refer to any other of these terms. Thus, the use of any of these terms individually should be considered as disclosure of all of the terms collectively, unless otherwise indicated.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present multiple core biopsy methods and systems have been described in the context of particularly preferred embodiments, the skilled artisan will appreciate, in view of the present disclosure, that certain advantages, features and aspects of the methods and systems may be realized in a variety of other applications, many of which have been noted above. Additionally, it is contemplated that various aspects and features of the various embodiments described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

Biopsy and Fidicial Marker Placement

One or more embodiments involve obtaining multiple biopsies through surgical or radiologic localization of a suspicious tumor within a solid organ or tissue that may be required for diagnosis and further profiling of a neoplasm/cancer with a further option for single or multiple marker placement. The marker(s) would be placed for the purposes of external beam radiation therapy, measurement of response (by measuring the distance between the markers), or marker placement for improved localization during surgical exploration and/or excision, for example and without limitation. In this embodiment the biopsy and marker placement could be performed in a single step, through a single pass resulting in multiple biopsies of different areas of the tumor in question, in addition to the placement of markers without the need for multiple skin entry punctures or multiple punctures through the target organ capsule. Furthermore within this embodiment, the coaxial system would also allow for injection of potentially thrombotic material through the biopsy tract in order to minimize bleeding and the potential for tumor tract seeding.

A typical procedure as per the aforementioned could be performed on a solid organ such as the lung, liver, kidney, bone, or lymph node (for example and without limitation) under imaging guidance (e.g., ultrasound, computed tomography, magnetic resonance imaging, functional imaging modalities [e.g., positron emission tomography]) or under directed visualization either due to the superficial nature or localizable nature of the lesion under physical examination or open surgical exposure.

In this embodiment it is assumed that the tumor may be localized under one of the described methods, although other suitable methods could be used. For the purposes of illustration, the example target would be a 2 cm lesion in the liver (14—FIG. 1), lung or kidney. The overlying skin (if applicable) of the patient 15 could be prepped and draped in a conventional surgical sterile field. Local anesthetic and/or moderate sedation (under intravenous anesthesia) or general anesthesia, for example, could then be initiated.

FIGS. 2-4, and FIG. 7 illustrate a first preferred embodiment of a biopsy and simultaneous fiducial marker system. The illustrated biopsy and simultaneous fiducial marker system or device 19 preferably includes an introducer 20 and biopsy needle 21.

The illustrated introducer 20 preferably includes a pair of coaxial elements, main shaft or cannula 10 and introducer body 1. The main shaft 10 may be constructed from stainless steel or other suitable materials. The main shaft 10 may have an outer diameter of 15 gauge, for example, that would be suitable for the example application. However, other suitable dimensions may be selected to suit other applications of the system. The introducer body 1 may be constructed from acetal (Delrin), ABS nylon, or other suitable polymers or other materials. The introducer body 1 may be fabricated from a variety of suitable fabrication techniques such as conventional machining, injection molding, or any other suitable process. The coaxial stylet 18 and stylet cap 17 preferably are removable from the introducer body 1.

Figure 4:
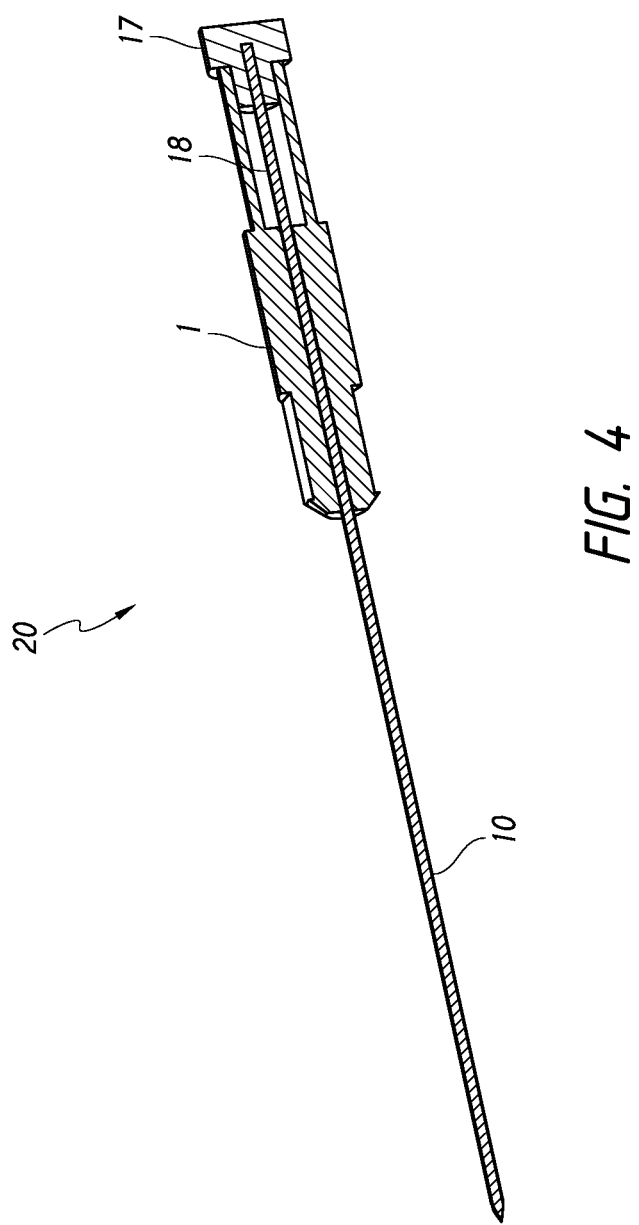
FIG. 4 is a cross-sectional view along the longitudinal axis of the introducer and stylet.

In use, the device can be removed from its packaging, with the cannula and the stylet 18 mated to one another, FIG. 4, to allow for a sharp single pass localization into the target tissue. The biopsy device 21 (with fiducial markers mounted, FIG. 7) can be armed through the retraction of the arming pins 7 in preparation of performing the simultaneous biopsy and fiducial placement. The tines 9 and biopsy trays 16 would at this point be fully retracted and armed.

Following appropriate exposure of the introducer tract with local anesthetic infiltration, if appropriate or desired, the introducer can be placed under aforementioned guidance to the target tumor, preferably in the proximal portion of the tumor i.e., closer to the cannula base).

The stylet 18 can be removed from the introducer body 1 and the biopsy needle 21, with fiducial marker (FIG. 7) can be inserted into the cannula utilizing the 'cheater device' (FIG. 6, step 4) or other appropriate component or method to urge the preshaped, curved ends of the tines 9 into a substantially linear orientation to permit introduction into the cannula. The biopsy device 21 can then be mated to the introducer 20 through a suitable connection, such as a threaded screw interface between the introducer body 1 and the adjusting collar 2. The radius of the biopsy (or radial spread of the tines 9) can be selected based on, for example, calibrated markers on the side of the biopsy device handle. Thus, the adjusting collar 2 can be utilized to adjust the biopsy device to a desired adjustment position for the tines 9, such as the 2 cm mark for example and without limitation. In the illustrated arrangement, the biopsy needle 21 is configured to allow a user to set the tines 9 spacing. As used herein, the "tine spacing" refers to a distance of movement of one or more of the tines 9 between a first position and a second position or a distance of one or more of the tines 9 from a specified location, such as the longitudinal axis of the device. For example, with the preshaped tines 9 as described herein, the tine spacing can be a radial distance or radius of an individual tine 9 or each of the tines 9 from the longitudinal axis of the device and/or an axial distance of an individual tine 9 or each of the tines 9 from an end of the cannula in a deployed position. In the illustrated arrangement, the tine spacing can be the radius of the end portions of each of the tines 9 (location of marker placement or location of biopsy) from the longitudinal axis of the device. Accordingly, with such an arrangement, all of the tines 9 can have substantially the same radius in the deployed position. Rotating the adjusting collar 2, relative to introducer body 1, permits a user to set the 3D position of the tines 9. The tines 9 preferably are constructed from shape memory material, such as NiTi so that the end portions of the tines 9 can be provided with a curved orientation to create distribution or spacing of the end portions (marker or biopsy portions) of the tines 9 in the deployed position. The end portions of the tines 9 can have substantially the same curvature or can have different curvatures from one another depending on the desired relative locations of the tines 9 upon deployment. In addition or in the alternative, the tines 9 can have the same or a similar length or can have different lengths to further adjust the dispersion or distribution of the sampling/marker placement locations. The anti-rotation bushing 13, or another suitable anti-rotation device, permits axial movement of the introducer body 1 relative to the housing 4 of the biopsy needle 21 and prevents rotation of introducer body 1 while rotating the adjusting collar 2. Preferably, the tines 9 are attached to slider 6 with adhesive or other suitable method. The tines 9 are configured to be coaxially movable within the cannula between an extended position and retracted position (not shown). The spring 12, or other suitable biasing member, in its relaxed configuration keeps the tines 9 in the extended position. The arming pins 7 are coupled to the slider 6 and permit a user to move the slider 6 proximally, whereby the spring 12 is compressed and the slider 6 engages with the split lock ring 11, or another suitable retention arrangement. This is the retracted position (not shown) for the tines 9. The trigger 8 and/or split ring 11 can be carried by a cap 5 of the device 19, which is coupled to an end of the housing 4 opposite the collar 2.

The biopsy trays 16 preferably are attached to the trigger 8 with adhesive or other suitable method. The biopsy tray wires are coaxial with the tines 9. Preferably, the overall lengths of the biopsy trays 16 are such that when the trigger 8 is depressed, the biopsy trays 16 extend beyond the distal end of the tines 9. The device biopsy trays 16 can be extended out from the tines 9 through the initial depression of the trigger 8 with simultaneous deployment of the fiducial markers 22 on the ends of the biopsy trays 16, to a desired position, such as the specified circumference defined by the tine spacing. Further depression on the trigger 8 results in the split lock ring 11 opening radially and release of the slider 6 and the tines 9 into their extended position, resulting in rapid deployment and simultaneous acquisition of, for example, one to four solid core biopsies. It will be appreciated that the biopsies may not occur precisely simultaneously due to a variety of reasons, such as normal manufacturing variations in the precise location of the biopsy spaces in the biopsy wires, for example. However, relative to prior art devices, the biopsies preferably occur at least substantially simultaneously.

The biopsy needle 21 can then be separated from the introducer 1 by unscrewing the adjusting collar 2, resulting in retraction of the tines 9, with biopsy stored in the biopsy tray 16 ready for removal from the tray for further processing, while leaving behind fiducial markers 22.

The biopsy device 21 can then be placed on a sterile field and re-armed. The trigger 8 can be depressed, without triggering the tine 9 deployment allowing for the biopsy tray 16 to be expressed and extraction/removal of the tissue sample to proceed. If desired, a lock arrangement can be provided to inhibit or prevent triggering of tine deployment for the purpose of tissue sample removal. The tissue sample can then be processed for diagnosis, additional stains, DNA testing, proteonomic analysis or further diagnostic investigations.

If desired, the biopsy needle 21 can then be reintroduced into the tumor for repeat biopsy and if additional regions or representations of tumor are desired, could be achieved through manipulating the introducer 1 either forward or back, altering the specified radius of biopsy or rotating the introducer, for example, 0-359 degrees allowing tines to sample new areas within the previous circumference or changing the circumference of the biopsy though previously described methods.

If desired, at near completion of the procedure the introducer 1 can be removed during simultaneous injection of thrombotic material such as autologous blood clot, embolic coils, gelfoam, thrombin, or the like. This is referred to as a "coaxial method" herein.

In this embodiment, for the illustrated application, the cannula size can range from 12-20 gauge with cannula length (not including handle) of 10-25 cm, with one or more and, preferably, two to four pre-shaped tines 9, and the markers 22 can be constructed of highly radiopaque materials such as stainless steel, platinum, memory alloy metals, gold, etc. Biopsy tray length can range from, for example, about 10 mm-20 mm and biopsy tray/sample core size can range from, for example, about 18-24 gauge. The diameter of separation of the most distal tines can range from, for example, about 1-10 cm, with more preferred range of 1-5 cm. These figures and materials are by way of example only.

Figure 5:
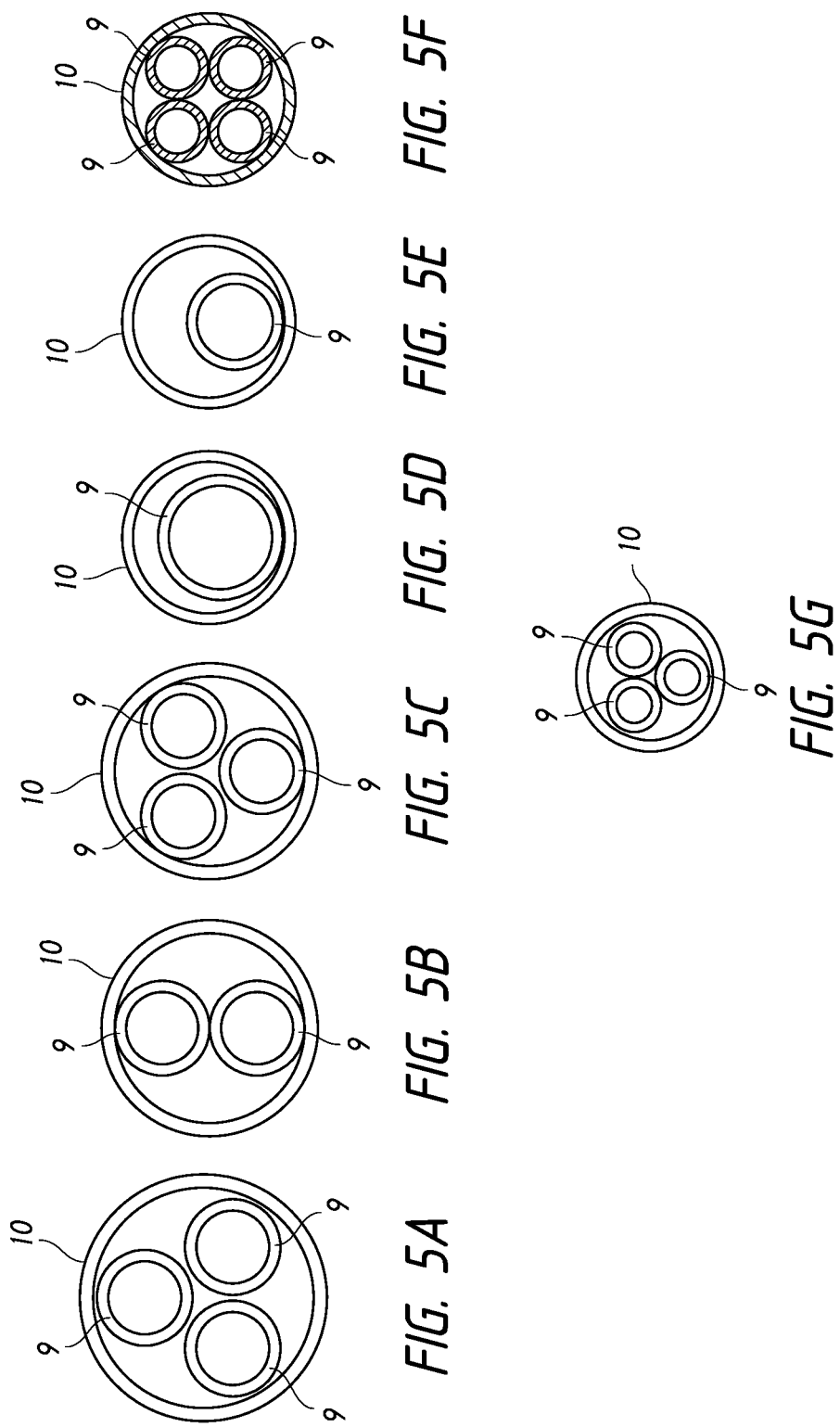
FIGS. 5A-5G are enlarged, cross-sectional views of the tines and trays, perpendicular to the longitudinal axis of FIG. 2, showing several alternative tine and introducer shaft or cannula combinations.

FIGS. 5A-5G illustrate various possible arrangements for the cannula 10 and tines 9. FIG. 5A illustrates a 14 gauge, ultrathin wall (0.083" OD×0.0745" ID) cannula 10 with three 21 gauge (0.032" OD×0.025" ID) tines 9. Such an arrangement can be used to obtain, for example, an approximately 0.6 mm core biopsy. FIG. 5B illustrates a 15 gauge, ultrathin wall (0.072" OD×0.0645" ID) cannula 10 with two 21 gauge (0.032" OD×0.025" ID) tines 9. Such an arrangement can be used to obtain, for example, an approximately 0.6 mm core biopsy. Depending on manufacturing tolerances, the size of the cannula 10 may need to be increased to accommodate the tines 9. FIG. 5C illustrates a 15 gauge, ultrathin wall (0.072" OD×0.0645" ID) cannula 10 with three 22 gauge (0.028" OD×0.020" ID) tines 9. Such an arrangement can be used to obtain, for example, an approximately 0.5 mm core biopsy. FIG. 5D illustrates a 17 gauge (0.058" OD×0.050" ID) cannula 10 with one 19 gauge (0.0425" OD×0.0325" ID) tine 9. Such an arrangement can be used to obtain, for example, an approximately 0.6 mm core biopsy. FIG. 5E illustrates a 17 gauge (0.058" OD×0.050" ID) cannula 10 with one 21 gauge (0.032" OD×0.025" ID) tine 9. Such an arrangement can be used to obtain, for example, an approximately 0.6 mm core biopsy. FIG. 5F illustrates a 17 gauge (0.058" OD×0.050" ID) cannula 10 with four 31 gauge (0.010" OD×0.005" ID) tines 9. Such an arrangement can be used to obtain, for example, an approximately 0.1 mm core biopsy. FIG. 5G illustrates an 18 gauge (0.050" OD×0.042" ID) cannula 10 with three 26 gauge (0.018" OD×0.012" ID) tines 9. Such an arrangement can be used for implanting fiducial markers without biopsy. These arrangements and dimensions of the cannula 10 and tines 9 are by way of example only.

With such an arrangement, the biopsy device and method permits distributed sampling/marker placement with a single puncture or placement of the device and in a non-serial process (e.g., simultaneously or substantially simultaneously). Distributed sampling/marker placement preferably involves a non-linear or non-axial distribution of multiple sampling/marker placement portions of the device resulting in non-linear or non-axial sampling/marker placement locations. For example, the sampling/marker placement locations can define a 2-D or circular distribution relative to one another and/or the longitudinal axis of the device or a 3-D or spherical distribution relative to one another and/or the longitudinal axis of the device. Although the illustrated device is configured to obtain a core tissue sample, alternative embodiments can be configured to perform aspiration biopsy utilizing hollow tubes (e.g., outer portions of the tines 9) with vacuum assistance, if desired.

Marker Placement Alone

In one embodiment, a known tissue target, (usually a tumor/neoplasm/cancer within a solid organ) with a further requirement for multiple marker placement for the purposes of external beam radiation therapy, measurement of response (by measuring the distance between the markers) or surgical exploration/excision. In this embodiment multiple markers could be placed in a non-linear fashion in a single step, through a single pass resulting in a spherical distribution of markers allowing for improved three dimensional localization, without the need for multiple skin entry punctures or multiple punctures through the target organ capsule. Furthermore if performed utilizing a coaxial method, would also allow for injection of potentially thrombotic material through the biopsy tract in order to minimize bleeding and the potential for tumor tract seeding.

A typical procedure as per the aforementioned method could be performed on a solid organ such as the lung, liver, kidney, bone, or lymph node under imaging guidance (e.g., ultrasound, computed tomography, magnetic resonance imaging, functional imaging modalities [e.g., positron emission tomography]) or under directed visualization either due to the superficial nature or localizable nature of the lesion under physical examination or open surgical exposure.

In this embodiment it is assumed that the tumor may be localized under one of the aforementioned methods or any other suitable method. For the purposes of illustration, the example target would be a 5 cm lesion in the liver, lung or kidney. The overlying skin (if applicable) would be prepped and draped in a conventional surgical sterile field. Either local anesthetic or moderate sedation (under intravenous anesthesia) or general anesthesia would then be initiated.

The device would be removed from its packaging, with the cannula and stylet 18 mated to one another, FIG. 4, to allow for sharp single pass localization into the target tissue. The fiducial deployment needle (with markers 22 mounted, FIG. 7), would then be armed through the retraction of the arming pins 7 in preparation of performing the fiducial placement. The needle carrying the markers 22 at this point preferably would be fully retracted.

Following appropriate exposure of the biopsy tract with local anesthetic infiltration, the introducer 1 will be placed under aforementioned or other suitable guidance to the target tumor, preferably in the proximal portion of the tumor (i.e., closer to the cannula base). In the case where a non-coaxial system is utilized, the marker placement device would be deployed itself (FIG. 8 or FIG. 9). FIG. 8 illustrates a hollow tine 9 with pusher 23. FIG. 9 illustrates a solid tine 25, which holds and deploys the marker 22.

Figure 6:
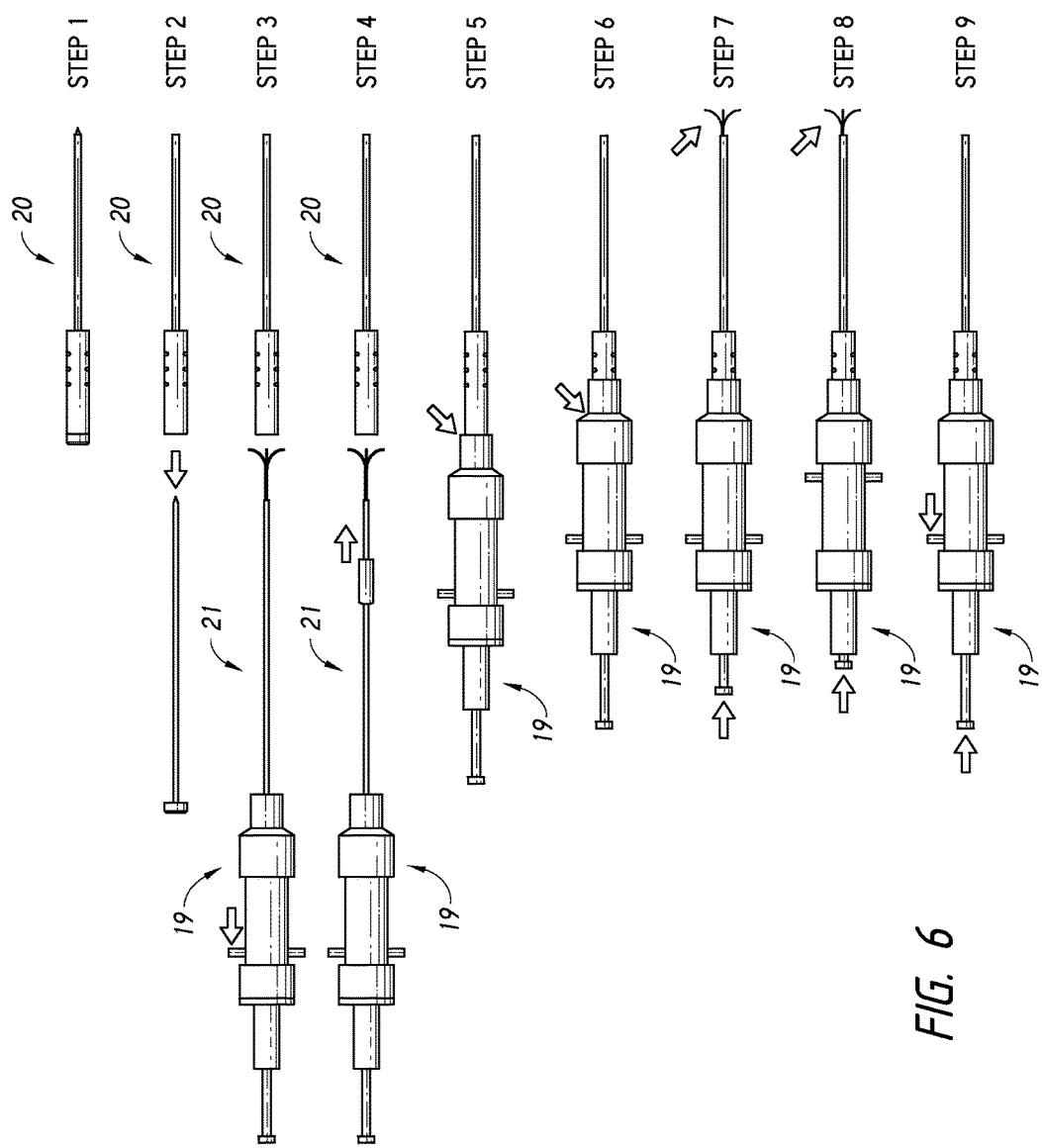
FIG. 6 is a schematic illustration of an exemplary biopsy and fiducial marker implantation procedure comprising nine identified steps, not all of which are necessarily used in all embodiments of the method. The steps are shown in an exemplary order, which can be varied in one or more embodiments of the method.
Figure 7A:
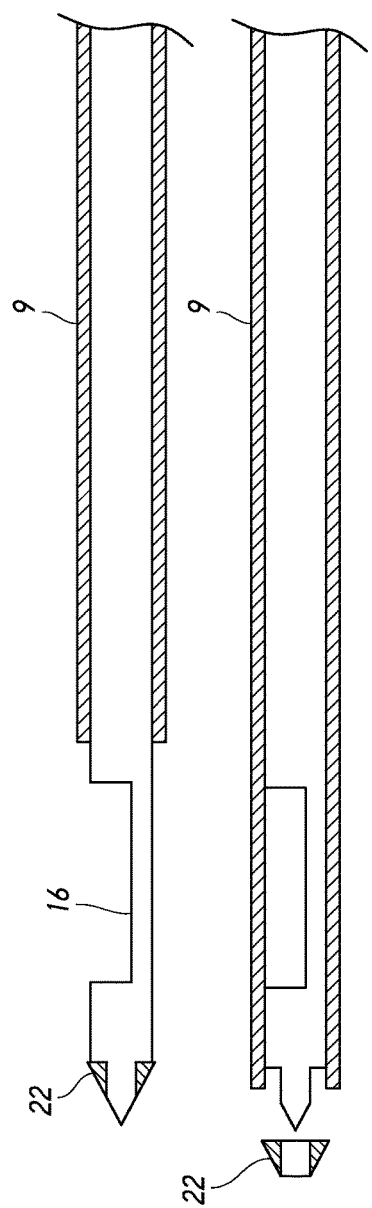
FIGS. 7A and 7B are enlarged, cross-sectional views of the distal end of alternative versions of the device of FIG. 2, showing fiducial marker placement.
Figure 7B:
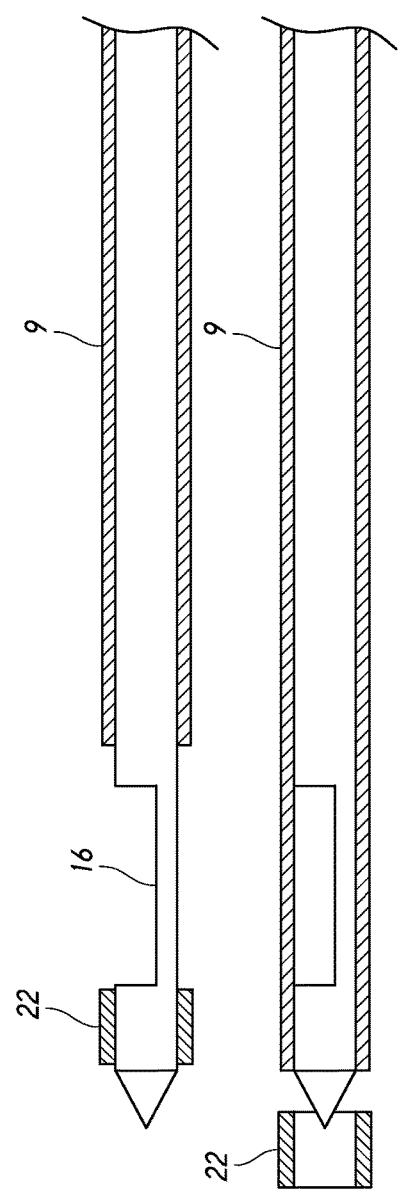

The stylet 18 (if using a coaxial system) would then be removed and marker device would be loaded onto the introducer 1 utilizing the 'cheater device' (FIG. 6, step 4). The biopsy device would then be mated to the introducer 1 through, for example, a threaded screw interface on the adjusting collar 2. The radius of the biopsy would then be chosen based on calibrated markers on the side of the biopsy device handle to, for example, the 2 cm mark. In the illustrated arrangement, the biopsy needle 21 is configured to allow a user to set the tines 9 spacing. Rotating the adjusting collar 2, relative to introducer body 1, permits a user to set the 3D position of the tines 9. The tines 9 preferably are constructed from shape memory material, such as NiTi. The anti-rotation bushing 13 prevents rotation of introducer body 1 while rotating the adjusting collar 2. The tines 9 are attached to slider 6 with adhesive or other suitable method. The tines 9 are configured to be coaxially movable between an extended position and retracted position (not shown). The spring 12 or other biasing member in its relaxed configuration keeps the tines 9 in the extended position. The arming pins 7 permits a user to move the slider 6 proximally, whereby the spring 12 is compressed and the slider 6 engages with the split lock ring 11 or other retention mechanism. This is the retracted position (not shown) for the tines 9. Regardless of whether coaxial or single needle system, the radius or diameter of the marker deployment relative to the longitudinal axis of the cannula (central axis) would then be chosen based on calibrated markers on the side of the device handle to, for example, the 3 cm mark.

The device would then be extended out through the initial depression of the trigger 8 resulting deployment of the fiducial markers 22 on the ends of the needle assembly, terminating at the specified circumference.

If in a coaxial form, the device would then be separated from the introducer 1 by unscrewing the adjusting collar 2, resulting in retraction of the tines 9, while leaving behind the fiducial markers 22.

In this embodiment, in view of the desired application, the cannula size could range from, for example, about 12-20 gauge, with two to four preshaped needles mounted with two to four fiducial markers, and length of cannula (not including handle) of 10-25 cm. Fiducial markers could be constructed of highly radiopaque materials such as stainless steel, platinum, memory alloy metals, gold, etc. Fiducial marker diameters could range from, for example, about 0.5 mm-1 mm in diameter, and length of, for example, about 2 mm-4 mm. These figures and materials are by way of example only.

Biopsy Alone

One embodiment involves obtaining multiple biopsies through surgical or radiologic localization of a suspicious tumor within a solid organ or tissue that may be required for diagnosis and further profiling of a neoplasm/cancer. In this embodiment multiple core biopsy samples could be obtained simultaneously or substantially simultaneously in a single step, through a single pass resulting in multiple biopsies of different areas of the tumor in question, in addition to the placement of markers without the need for multiple skin entry punctures or target organ capsule puncture. The coaxial configuration would also allow for injection of potentially thrombotic material through the biopsy tract in order to minimize bleeding and the potential for tumor tract seeding.

A typical procedure as per the aforementioned could be performed on a solid organ such as the lung, liver, kidney, bone, or lymph node under imaging guidance (e.g., ultrasound, computed tomography, magnetic resonance imaging, functional imaging modalities [e.g., positron emission tomography]) or under directed visualization either due to the superficial nature or localizable nature of the lesion under physical examination or open surgical exposure.

In this embodiment it is assumed that the tumor may be localized under one of the aforementioned methods or another suitable method. For the purposes of illustration, the example target would be a 6 cm lesion in the kidney. The overlying skin (if applicable) would be prepped and draped in a conventional surgical sterile field. Local anesthetic and/or moderate sedation (under intravenous anesthesia) or general anesthesia would then be initiated.

The device would be removed from its packaging, with the cannula and the stylet 18 mated to one another, FIG. 4, to allow for a sharp single pass localization into the target tissue. The biopsy device 21 would then be armed through the retraction of the arming pins 7 in preparation of performing the biopsy. The tines 9 and biopsy trays 16 would at this point be fully retracted and armed.

Following appropriate exposure of the introducer tract with local anesthetic infiltration, the introducer 1 will be placed under aforementioned guidance to the target tumor, in the proximal portion of the tumor i.e., closer to the cannula base).

The stylet 18 would then be removed and biopsy needle 21, with fiducial marker (FIG. 7) would be inserted into the cannula utilizing the 'cheater device' (FIG. 6, step 4). The biopsy device 21 would then be mated to the introducer 20 through, for example, a threaded screw interface on the adjusting collar 2. The radius of the biopsy would then be chosen based on calibrated markers on the side of the biopsy device handle to, for example, the 6 cm mark. In the illustrated arrangement, the biopsy needle 21 is configured to allow a user to set the tines 9 spacing. Rotating the adjusting collar 2, relative to introducer body 1, permits a user to set the 3D position of the tines 9. The tines 9 preferably are constructed from shape memory material, such as NiTi, to have a curved end portion. The anti-rotation bushing 13 prevents rotation of introducer body 1 while rotating the adjusting collar 2. The tines 9 are attached to slider 6 with adhesive or other suitable method. The tines 9 are configured to be coaxially movable between an extended position and retracted position (not shown). The spring 12 or other biasing member in its relaxed configuration keeps the tines 9 in the extended position. The arming pins 7 permits a user to move the slider 6 proximally, whereby the spring 12 is compressed and the slider 6 engages with the split lock ring 11 or other retention mechanism. This is the retracted position (not shown) for the tines 9.

The biopsy trays 16 are attached to the trigger 8 with adhesive or other suitable method. The biopsy tray wires are coaxial with the tines 9. Preferably, the overall lengths of the biopsy tray 16 are such that when the trigger 8 is depressed, the biopsy trays 16 extend beyond the distal end of the tines 9. The device biopsy trays 16 would be extended out through the initial depression of the trigger 8 to the specified circumference. Further depression on the trigger 8 will result in the split lock ring 11 to open radially and release the slider 6 and the tines 9 into their extended position, resulting in rapid deployment and simultaneous acquisition of one to four solid core biopsies.

The biopsy needle 21 would then be separated from the introducer 1 by unscrewing the adjusting collar 2, resulting in retraction of the tines 9, with biopsy stored in the biopsy tray 16 ready for removal from the tray for further processing.

The biopsy device 21 could then be placed on a sterile field and re-armed. The trigger 8 could then be depressed, without triggering the tine 9 deployment (as described above) allowing for the biopsy tray 16 to be expressed and extraction/removal of the tissue sample to proceed. The tissue sample could then be processed for diagnosis, additional stains, DNA testing, proteonomic analysis or further diagnostic investigations.

The biopsy needle 21 could then be reintroduced into the tumor for repeat biopsy and if additional regions or representations of tumor are desired, could be achieved through manipulating the introducer 1 either forward or back, altering the specified radius of biopsy or rotating the introducer, for example, 0-359 degrees allowing tines to sample new areas within the previous circumference or changing the circumference of the biopsy though previously described methods.

At near completion of the procedure the cannula could then be removed during simultaneous injection of thrombotic material such as autologous blood clot, embolic coils, gelfoam, thrombin, or the like.

In this embodiment, in view of the described application, the cannula size could range from, for example, about 12-20 gauge with cannula length (not including handle) of 10-25 cm, with two to four preshaped tines. Biopsy tray length could range from, for example, about 10 mm-20 mm and biopsy tray/sample core size could range from, for example, about 18-24 gauge. These figures and materials are by way of example only.

Biopsy and Targeted Local Therapy

One embodiment involves obtaining multiple biopsies through surgical or radiologic localization of a suspicious tumor within a solid organ or tissue that may be required for diagnosis and further profiling of a neoplasm/cancer. In this embodiment multiple core biopsy samples could be obtained simultaneously or substantially simultaneously in a single step, through a single pass resulting in multiple biopsies of different areas of the tumor in question, optionally in addition to the placement of markers, without the need for multiple skin entry punctures or target organ capsule puncture. The coaxial configuration would also allow for injection of potentially thrombotic material through the biopsy tract in order to minimize bleeding and the potential for tumor tract seeding.

A typical procedure as per the aforementioned could be performed on a solid organ such as the lung, liver, kidney, bone, or lymph node under imaging guidance (e.g., ultrasound, computed tomography, magnetic resonance imaging, functional imaging modalities [e.g., positron emission tomography]) or under directed visualization either due to the superficial nature or localizable nature of the lesion under physical examination or open surgical exposure.

In this embodiment it is assumed that the tumor may be localized under one of the aforementioned methods or another suitable method. For the purposes of illustration, the example target would be, for example, a 6 cm lesion in the kidney. The overlying skin (if applicable) would be prepped and draped in a conventional surgical sterile field. Local anesthetic and/or moderate sedation (under intravenous anesthesia) or general anesthesia would then be initiated.

The device would be removed from its packaging, with the cannula and the stylet 18 mated to one another, FIG. 4, to allow for a sharp single pass localization into the target tissue. The biopsy device 21 would then be armed through the retraction of the arming pins 7 in preparation of performing the biopsy. The tines 9 and biopsy trays 16 would at this point be fully retracted and armed.

Following appropriate exposure of the introducer tract with local anesthetic infiltration, the introducer 1 will be placed under aforementioned guidance to the target tumor, preferably in the proximal portion of the tumor (i.e., closer to the cannula base).

The stylet 18 would then be removed and biopsy needle 21, with optional fiducial marker (FIG. 7) would be inserted into the cannula utilizing the 'cheater device' (FIG. 6, step 4). The biopsy device 21 would then be mated to the introducer 20 through a threaded screw interface on the adjusting collar 2. The radius of the biopsy would then be chosen based on calibrated markers on the side of the biopsy device handle to, for example, the 6 cm mark. In the illustrated arrangement, the biopsy needle 21 is configured to allow a user to set the tines 9 spacing. Rotating the adjusting collar 2, relative to introducer body 1, permits a user to set the 3D position of the tines 9. The tines 9 preferably are constructed from shape memory material, such as NiTi, to have a curved end portion. The anti-rotation bushing 13 prevents rotation of introducer body 1 while rotating the adjusting collar 2. The tines 9 are attached to slider 6 with adhesive or other suitable method. The tines 9 are configured to be coaxially movable between an extended position and retracted position (not shown). The spring 12 or other biasing element in its relaxed configuration keeps the tines 9 in the extended position. The arming pins 7 permits a user to move the slider 6 proximally, whereby the spring 12 is compressed and the slider 6 engages with the split lock ring 11 or other retention mechanism. This is the retracted position (not shown) for the tines 9.

The biopsy trays 16 are attached to the trigger 8 with adhesive or other suitable method. The biopsy tray wires are coaxial with the tines 9. Preferably, the overall lengths of the biopsy tray 16 are such that when the trigger 8 is depressed, the biopsy trays 16 extend beyond the distal end of the tines 9. The device biopsy trays 16 would be extended out through the initial depression of the trigger 8 to the specified circumference. Further depression on the trigger 8 will result in the split lock ring 11 to open radially and release the slider 6 and the tines 9 into their extended position, resulting in rapid deployment and simultaneous or substantially simultaneous acquisition of one to four solid core biopsies.

The biopsy needle 21 could then be separated from the introducer 1 by unscrewing the adjusting collar 2, resulting in retraction of the tines 9, with biopsy stored in the biopsy tray 16 ready for removal from the tray for further processing.

The biopsy device 21 could then be placed on a sterile field and re-armed. The trigger 8 could then be depressed, without triggering the tine 9 deployment allowing for the biopsy tray 16 to be expressed and extraction/removal of the tissue sample to proceed. The tissue sample could then be processed for diagnosis, additional stains, DNA testing, proteonomic analysis or further diagnostic investigations.

The biopsy needle 21 could then be reintroduced into the tumor for repeat biopsy and if additional regions or representations of tumor are desired, could be achieved through manipulating the introducer 1 either forward or back, altering the specified radius of biopsy or rotating the introducer, for example, 0-359 degrees allowing tines to sample new areas within the previous circumference or changing the circumference of the biopsy though previously described methods.

At near completion of the procedure the introducer 1 could then be removed during simultaneous injection through the cannula of targeted therapies including radioactive sources, chemotherapy, thermal ablation device, electrical ablation device, stem cells, immunological agents, biologically active therapies, chemicals, embolic or other types of biologically active materials.

Alternatively, the introducer 1 could be utilized as a conduit to the biopsy area and a separate device similar to the previously-described device 19 could be used to distribute therapy via a coaxial technique. In another alternative arrangement, the device 19 could be provided with conduits to allow both biopsy and distribution of therapy (and optional marker placement) with the same device 19. In some such arrangements, each individual tine 9 can be configured for performing both the biopsy and distribution of therapy. Alternatively, individual tines 9 could be specialized for one or the other of biopsy and distribution of therapy. Preferably, at least the biopsy tines 9 could also be configured to deploy a marker; however, any of the specialized tines 9 could be configured for marker placement in addition to another function.

In this embodiment, in view of the described application, the cannula size could range from, for example, about 12-20 gauge with cannula length (not including handle) of, for example, about 10-25 cm, with two to four preshaped tines. Biopsy tray length could range from, for example, about 10 mm-20 mm and biopsy tray/sample core size could range from, for example, about 18-24 gauge. These figures and materials are by way of example only.

Marker and Targeted Local Therapy

An embodiment involves a known tissue target, (usually a tumor/neoplasm/cancer within a solid organ) with a further requirement for multiple marker placement for the purposes of external beam radiation therapy, measurement of response (by measuring the distance between the markers) or surgical exploration/excision. In this embodiment multiple markers could be placed in a non-linear fashion in a single step, through a single pass resulting in, for example, a spherical distribution of markers allowing for improved three dimensional localization, without the need for multiple skin entry punctures or multiple punctures through the target organ capsule, such as by a method and via a device substantially as described above. Furthermore if performed utilizing a coaxial method, such an embodiment would also allow for injection of potentially thrombotic material through the biopsy tract in order to minimize bleeding and the potential for tumor tract seeding.

A typical procedure as per the aforementioned method could be performed on a solid organ such as the lung, liver, kidney, bone, or lymph node under imaging guidance (e.g., ultrasound, computed tomography, magnetic resonance imaging, functional imaging modalities [e.g., positron emission tomography]) or under directed visualization either due to the superficial nature or localizable nature of the lesion under physical examination or open surgical exposure.

In this embodiment it is assumed that the tumor may be localized under one of the aforementioned methods or another suitable method. For the purposes of illustration, the example target would be, for example, a 5 cm lesion in the liver, lung or kidney. The overlying skin (if applicable)

would be prepped and draped in a conventional surgical sterile field. Either local anesthetic or moderate sedation (under intravenous anesthesia) or general anesthesia would then be initiated.

The device would be removed from its packaging, with the cannula and stylet 18 mated to one another, FIG. 4, to allow for sharp single pass localization into the target tissue. The fiducial deployment needle (with markers 22 mounted, FIG. 7), would then be armed through the retraction of the arming pins 7 in preparation of performing the fiducial placement. The needle carrying the markers 22 at this point would be fully retracted.

Following appropriate exposure of the biopsy tract with local anesthetic infiltration, the introducer 1 will be placed under aforementioned guidance to the target tumor, preferably in the proximal portion of the tumor (i.e., closer to the cannula base). In the case where a non-coaxial system is utilized, the marker placement device would be deployed itself (FIG. 8 or FIG. 9).

The stylet 18 (if using a coaxial system) would then be removed and marker device would be loaded onto the introducer 1 utilizing the 'cheater device' (FIG. 6, step 4). The biopsy device would then be mated to the introducer 1 through, for example, a threaded screw interface on the adjusting collar 2. The radius of the biopsy would then be chosen based on calibrated markers on the side of the biopsy device handle to, for example, the 2 cm mark. In the illustrated arrangement, the biopsy needle 21 is configured to allow a user to set the tines 9 spacing. Rotating the adjusting collar 2, relative to introducer body 1, permits a user to set the 3D position of the tines 9. The tines 9 preferably are constructed from shape memory material, such as NiTi, to have a curved end portion. The anti-rotation bushing 13 prevents rotation of introducer body 1 while rotating the adjusting collar 2. The tines 9 are attached to slider 6 with adhesive or other suitable method. The tines 9 are configured to be coaxially movable between an extended position and retracted position (not shown). The spring 12, or other biasing element, in its relaxed configuration keeps the tines 9 in the extended position. The arming pins 7 permits a user to move the slider 6 proximally, whereby the spring 12 is compressed and the slider 6 engages with the split lock ring 11 or other retention mechanism. This is the retracted position (not shown) for the tines 9. Regardless of whether coaxial or single needle system, the radius or diameter of the marker deployment relative to the plane of the cannula (central axis) would then be chosen based on calibrated markers on the side of the device handle to, for example, the 3 cm mark.

The device would then be extended out through the initial depression of the trigger 8 resulting deployment of the fiducial markers 22 on the ends of the needle assembly, terminating at the specified circumference.

If in a coaxial form, the device could then be separated from the introducer 1 by unscrewing the adjusting collar 2, resulting in retraction of the tines 9, while leaving behind the fiducial markers 22.

At near completion of the procedure the introducer 1 could then be removed during simultaneous injection through the cannula of targeted therapies including radioactive sources, chemotherapy, thermal ablation device, electrical ablation device, stem cells, immunological agents, biologically active therapies, chemicals, embolic or other types of biologically active materials. Alternatively, the cannula could be utilized as a conduit to the fiducial placement area and a separate device similar to the above-described device 19 could be used to distribute therapy via a coaxial technique.

Alternatively the fiducial markers 22 could be radioactive thus allowing for locoregional brachytherapy to be performed in the target area. Utilizing the coaxial technique, multiple assemblies with multiple radioactive fiducials markers 22 could be placed to allow for optimal geometric placement of the radioactive fiducials (eg brachytherapy seeds) in solid organs such as the prostate. Furthermore refinements of this method (or other methods described herein) may allow for the use of three dimensional mapping of a target area through navigation software/systems that could be coupled with the tines on a collective or, preferably, an individual basis. Motorized deployment of the tines through computer guided navigation could then be utilized to deploy individual brachytherapy seeds simultaneously or in sequence through a single introducer 1 into a larger volume in a non-symmetrical fashion in areas such as the prostate. For example, the tines could be collectively or, preferably, individually coupled to a drive device (e.g., a motor) and operated via a controller. In some arrangements, the controller can receive feedback regarding the positioning of the tines and can utilize such information in controlling the movement of the tines. The inner and outer portions of the tines (if present in a particular embodiment) can be driven together or separately. Motorized or computer-aided movement of the tines can be applied to any of the embodiments/methods described herein, or other similar embodiments/methods.

In this embodiment, in view of the described application, the cannula size could range from, for example, 12-22 gauge, with two to four preshaped needles mounted with two to four fiducial markers, and length of cannula (not including handle of 10-25 cm. Fiducial markers could be constructed of highly radiopaque materials such as stainless steel, platinum, tantalum, memory alloy metals, gold, etc. with radioactive sources such as radium-226, cesium-137, cobalt-60, iridium-192, iodine-125, gold-198 and palladium-103. Fiducial marker diameters could range from, for example, about 0.5 mm-1 mm in diameter, and length of, for example, about 2 mm-4 mm. These figures and materials are by way of example only.

Marker Placement

Figure 10:
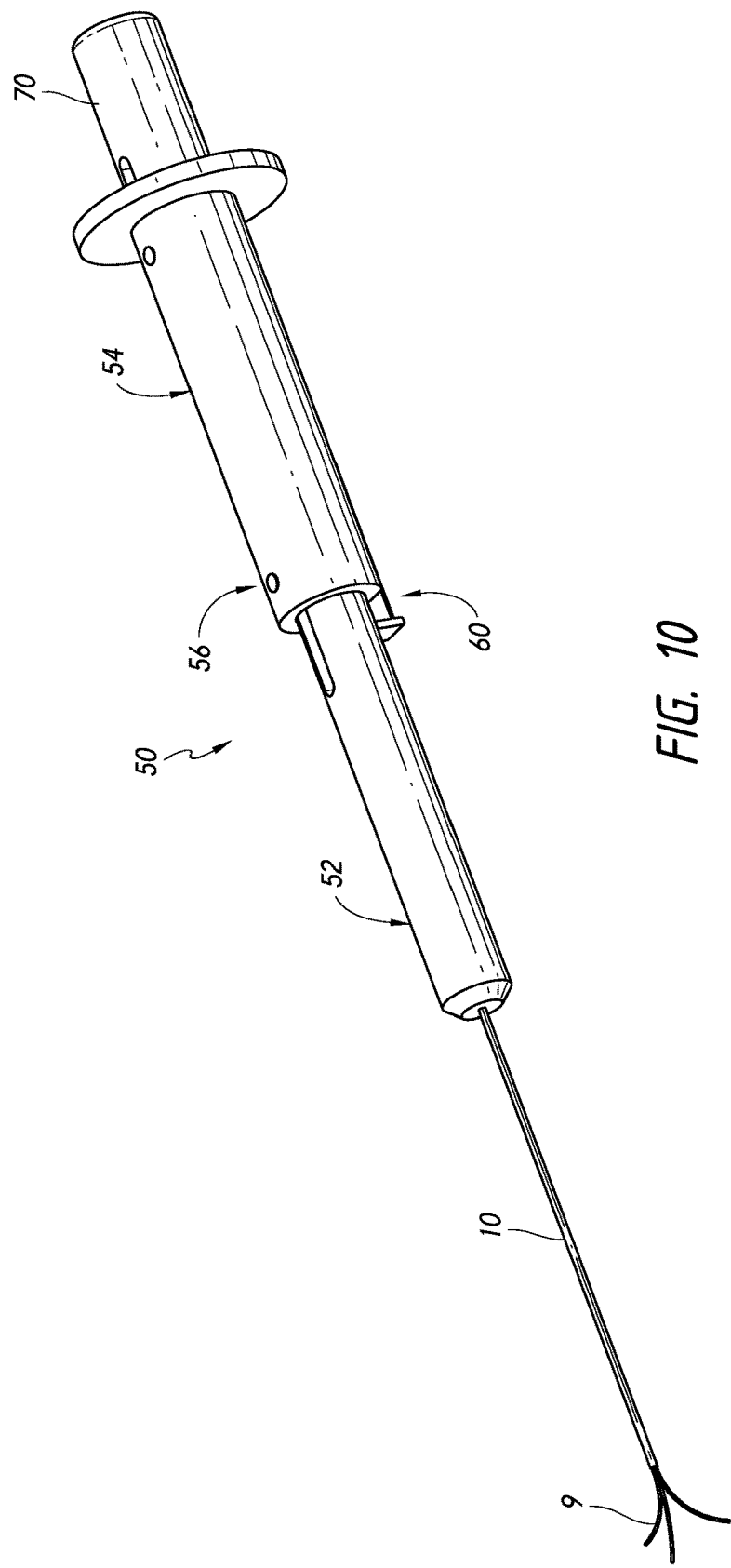
FIG. 10 is a perspective view of a fiducial marker placement apparatus.
Figure 11:
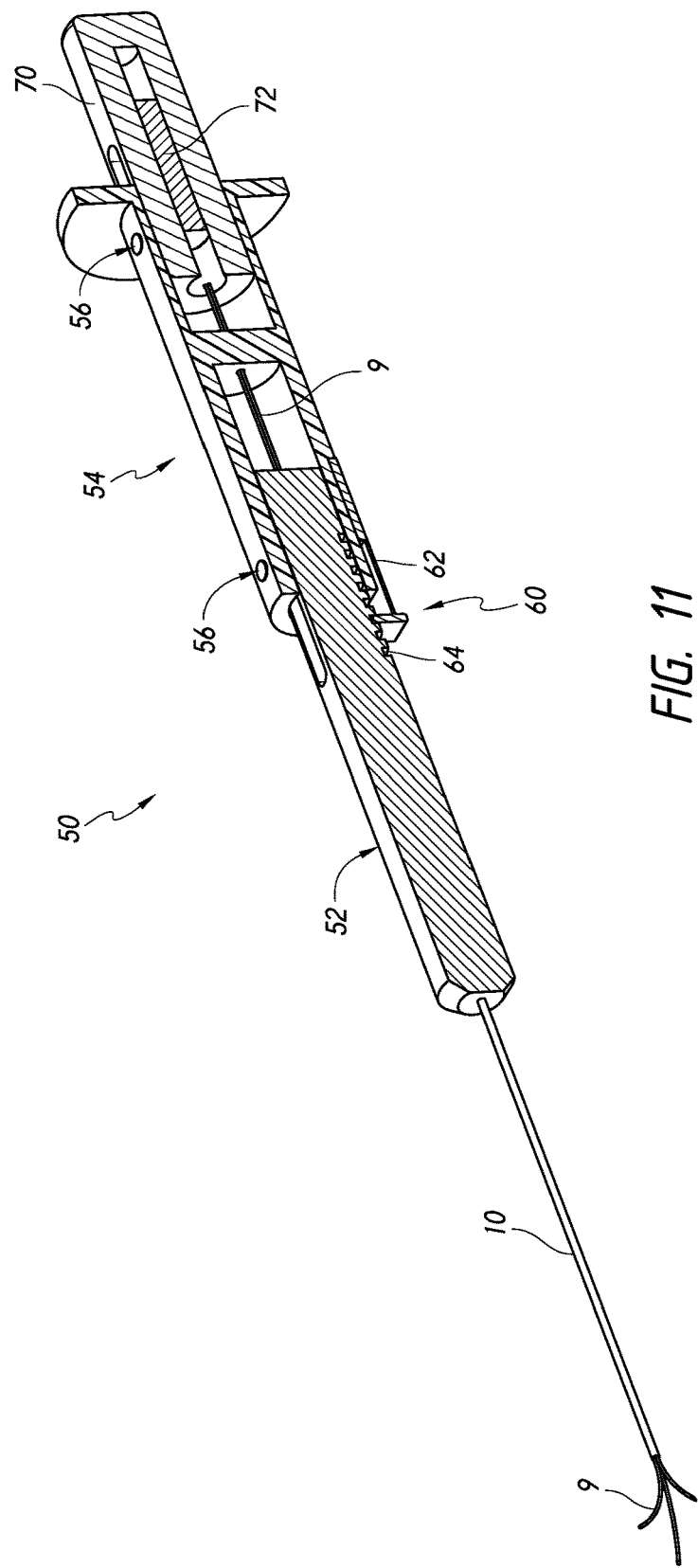
FIG. 11 is a cross-sectional view along the longitudinal axis of the fiducial marker placement apparatus of FIG. 10.

FIGS. 10 and 11 illustrate an apparatus or device for fiducial marker (or other marker or object) placement, which is similar in one or more respects to the other devices disclosed herein. Preferably, the apparatus permits placement of multiple fiducial markers with a single puncture of the patient's skin, organ or other anatomical location. The illustrated apparatus provides for simultaneous or substantially simultaneous placement of multiple fiducial markers. The fiducial markers can be placed in a scattered or dispersed formation or configuration, such as in a two-dimensional or three-dimensional configuration. Preferably, the fiducial markers are placed at spaced locations from a longitudinal axis of the apparatus, as described above with respect to other devices disclosed herein.

The illustrated apparatus preferably provides for marker placement, among other possible functions, without biopsy functionality. Such an arrangement can have fewer parts and can be less expensive to manufacture compared to an embodiment that also provides biopsy functionality. Thus, such an arrangement can provide the advantages associated with multiple marker placement as described herein at a lower cost and may be preferable for applications in which biopsy is not necessary or desired.

The illustrated apparatus includes a body or handle 50 having a first portion 52 and a second portion 54. The first portion 52 may be similar to the introducer 1 of the above-described embodiments and preferably includes a main shaft or cannula 10 extending in a longitudinal direction in a direction opposite the second portion 54. In some configurations, the cannula 10 can be sized or otherwise configured to be introduced into the anatomy of a patient without the use of a stylet, which is described in connection with the above embodiments and methods. For example, the cannula 10 can be an 18 gauge needle, or of a similar or smaller cross-sectional dimension, such that it can be introduced on its own. In at least some configurations, eliminating the biopsy functionality permits such sizing of the cannula 10. Advantageously, such an arrangement can permit the apparatus to be introduced into the patient's anatomy as an assembled unit instead of utilizing post-insertion or post-puncture assembly as described in other embodiments herein.

The first and second portions 52 and 54 of the handle 50 can be generally cylindrical in shape or otherwise configured to be held by a user of the apparatus. The first portion 52 and second portion 54 preferably are telescopically engaged with one another such that an overall longitudinal length or relative longitudinal position of the body or handle 50 can be adjusted. Preferably, the first portion 52 and second portion 54 are constrained from rotation relative to one another, such as by the illustrated pin-and-slot arrangement 56 or another suitable arrangement.

Preferably, the handle 50 includes an adjuster or lock arrangement 60 that permits the first and second portions 52 and 54 to be secured in a selected one of a plurality of available relative longitudinal positions. Similar to embodiments described above, such an arrangement permits adjustment of a deployment distance (e.g., radius) of the fiducial markers. In the illustrated arrangement, the lock arrangement 60 comprises a latch 62 that can be engaged in a selected one of several slots, notches or recesses 64. The latch 62 can be a resilient arm with an engagement member that engages the recesses 64, for example. A latch-type lock arrangement is advantageous because it provides a reliable, low-cost locking functionality. However, other suitable arrangements could also be used, such as a threaded engagement as described above or any other suitable structure.

At least one tine 9, preferably multiple tines 9, are positioned within the cannula 10 and handle 50. The tines 9 can be similar to those described above and may be, for example, tubular members constructed partially or entirely from a shape memory material, such as NiTi, so that the end portions of the tines 9 can be provided with a non-linear (e.g., curved) orientation to create distribution or spacing of the end portions (marker portions) of the tines 9 in the deployed position. The end portions of the tines 9 can have substantially the same curvature or can have different curvatures from one another depending on the desired relative locations of the tines 9 upon deployment. In addition or in the alternative, the tines 9 can have the same or a similar length or can have different lengths to further adjust the dispersion or distribution of the sampling/marker placement locations.

The tines 9 preferably extend into a hollow interior of the second portion 54 of the handle 50 and are coupled for movement with or can otherwise be actuated by a trigger or button 70. In the illustrated arrangement, the tines 9 are longitudinally movable by the trigger or button 70. In other configurations, a button or trigger can actuate the tines, which can be secured to another member, which can be manually or otherwise driven (e.g., spring-loaded or motorized). In the illustrated arrangement, the trigger or button 70 is manually driven (e.g., moved in a longitudinal direction) to deploy the end portions of the tines 90 from the cannula 10 towards or to a deployment position. The trigger or button 70 can be rotationally fixed and limited in movement relative to the second portion 54 of the handle 50 by a suitable arrangement, such as a pin-and-slot arrangement 56. Once the tines 9 are deployed, fiducial markers (not shown—see FIGS. 12A and 12B) can be deployed from the tines 9 and placed into the patient's anatomy. Preferably, the deployment of the fiducial markers can be simultaneous or substantially simultaneous.

The fiducial markers can be separated or deployed from the tines 9 in any suitable manner. The markers could be separated as a result of retraction of the tines 9, such as retraction from the deployed position. However, preferably the markers are actively deployed or separated from the tines 9. For example, an additional member or additional members (e.g., wires) can be provided to contact and separate the markers from the tines 9. The wires can be coaxially positioned within the tines 9 in some configurations. In the illustrated arrangement, the button or trigger 70 is also operational to move or actuate the wires (not shown) that deploy or separate the markers from the tines 9. Preferably, the markers are carried within end portions of the tines 9 and the wires are coaxially positioned within the tines 9. A deployment member 72 is configured to be actuated by the button or trigger 70 and to move the wires to deploy the markers from the end portions of the tines 9.

In use, a tumor or other anatomical structure or region may be localized under one of the aforementioned methods or another suitable method. The skin overlying the target (if applicable) would be prepped and draped in a conventional surgical sterile field. Either local anesthetic or moderate sedation (under intravenous anesthesia) or general anesthesia) could then be initiated.

The apparatus could be removed from its packaging and, if necessary or desired, adjusted to a desired deployment distance by adjusting the relative position of the first portion 52 and the second portion 54 of the handle 50 utilizing, for example, the lock arrangement 60. The cannula 10 can be utilized for a single pass localization into the target tissue, preferably without the use of a stylet. The tines 9 and deployment wires or other structures that deploy the markers at this point preferably would be fully retracted.

The button or trigger 70 can be pressed toward or into the handle 50 to deploy the end portions of the tines 9 to an extended or deployment position. Preferably, the button or trigger 70 eventually contacts the deployment member 72 and moves the deployment member 72 along the longitudinal axis of the apparatus thereby moving the deployment wires or other structures to separate or deploy the markers from the tines 9 at the desired locations (e.g., circumference). The tines 9 and deployment wires can be retracted into the cannula 10 manually or otherwise (e.g., via biasing of the button or trigger 70) and the apparatus removed from the patient. As described above, the apparatus could be used multiple times to place multiple sets of markers. The apparatus could be removed between deployments or can be repositioned between deployments, with multiple rounds of markers provided within the tines 9.

Example Markers

Figure 12A:
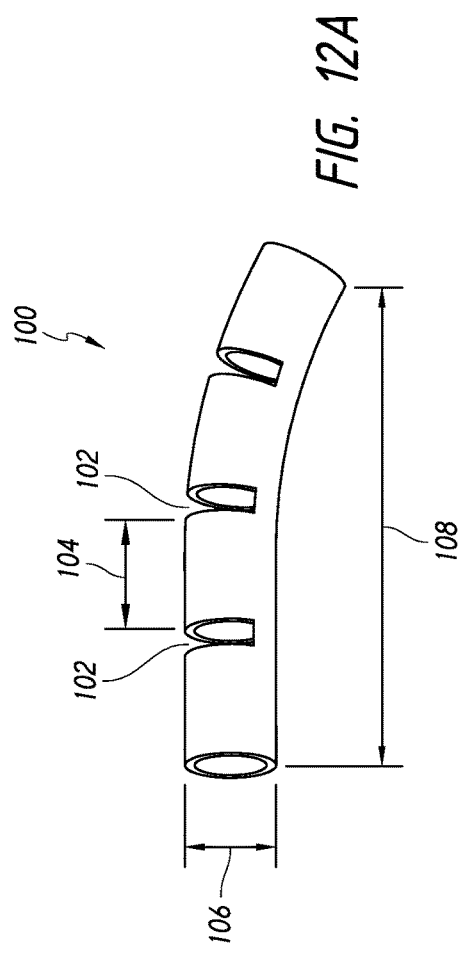
FIGS. 12A and 12B illustrate fiducial markers that can be used with the fiducial marker placement apparatus of FIGS. 10 and 11, as well as other marker placement devices, such as those disclosed herein.
Figure 12B:
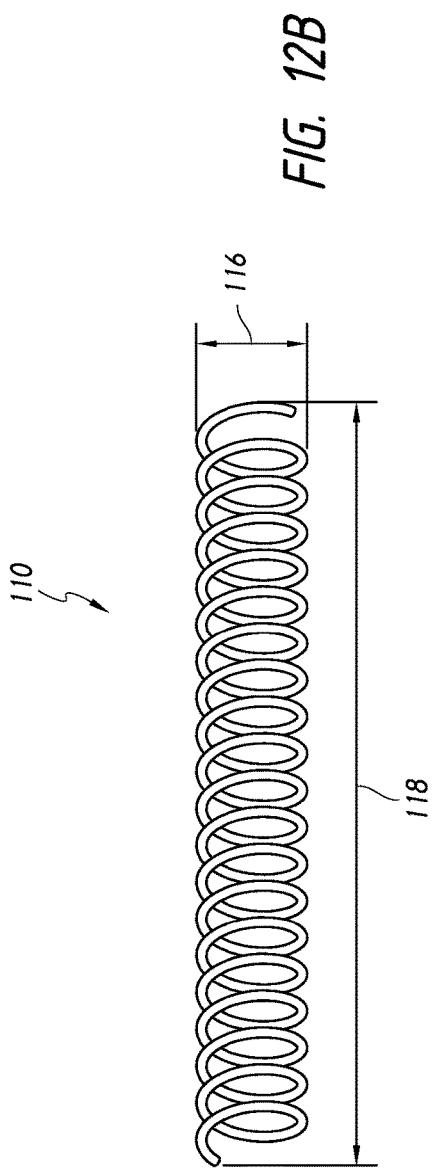

FIGS. 12A and 12B illustrate embodiments of fiducial markers that can be used, for example, with the devices disclosed herein. As described above, the fiducial markers can be constructed partially or entire from a highly radiopaque material, such as tantalum, any other materials disclosed herein or any other suitable materials.

The marker 100 of FIG. 12A comprises a generally solid rod of material with one or more cuts or notches 102 provided in a radial direction. Preferably, a number of cuts or notches 102 are provided and can be spaced apart from one another a distance 104 selected to allow the marker to generally conform to the non-linear shape of the tine 9 in which the marker is placed. For example, in the illustrated arrangement, three cuts or notches can be provided in a marker having a length 108 of about 5 mm to about 15 mm, for example and without limitation. Thus, notch spacing can be between about 1-1.25 mm to about 3.75 or 4 mm, for example. Notch spacing could also be smaller or larger, or any value within the specified range or any smaller or larger value. In addition, a diameter or cross-sectional dimension 106 of the marker can be selected such that the marker can be accommodated within the tine 9, such as between about 0.016 inch and about 0.040 inch, for example and without limitation. The diameter or cross-sectional dimension could also be smaller or larger, or any value within the specified range or any smaller or larger value. The cuts or notches 102 preferably extend a radial distance through the cross-section of the marker 100 to provide a desired level of flexibility to the marker 100. For example, the cuts or notches 102 can extend about 70% to about 90% of the diameter or cross-sectional dimension of the marker. The cuts or notches 102 could also extend a lesser or greater radial distance, or any value within the specified range or lesser or greater value.

The marker 110 of FIG. 12B is or comprises a coiled wire of a suitable material, such as those disclosed herein. The marker 110 of FIG. 12B can have overall dimensions (e.g., overall diameter or cross-sectional dimension 116 or length 118) the same as or similar to the marker of FIG. 12A. The wire size (diameter) of the coiled wire can be any suitable dimension to provide the marker with the desired properties, such as flexibility or bending along the longitudinal axis, for example and without limitation. In some configurations, the wire size can be between about 0.005 inch and about 0.010 inch. The wire size could also be smaller or larger, or any value within the specified range or any smaller or larger value.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present three-dimensional multiple core biopsy with simultaneous fiducial marker placement devices and methods has been described in the context of particularly preferred embodiments, the skilled artisan will appreciate, in view of the present disclosure, that certain advantages, features and aspects of the system may be realized in a variety of other applications, many of which have been noted above. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. A method of accessing multiple locations within an organ or tissue, comprising:
   positioning an introducer at a desired location within the organ or tissue;
   removing a stylet from the introducer;
   coupling an access device to the introducer;
   adjusting the access device to a selected deployment distance;
   simultaneously or substantially simultaneously deploying inner portions of multiple tines the deployment distance such that distal end portions of each of the inner portions are distributed at spaced locations from one another, wherein the deploying of the inner portions of the tine assemblies comprises pressing a trigger of a biopsy device and wherein the inner portions are directly coupled to the trigger;
   using the multiple tines to obtain tissue samples and deploy fiducial markers, wherein each fiducial marker has a rod shape with a plurality of notches in the radial direction of the each fiducial marker, and wherein each notch of the plurality of notches extends between 70% to 90% of a diameter of the each fiducial marker.

2. The method of claim 1, wherein the using the multiple tines further comprises delivering therapeutics with one or more of the multiple tines.

3. The method of claim 1, wherein the deployment distance of each of the multiple tines is identical or substantially identical.

4. The method of claim 3, wherein the deployment distance of each of the multiple tines is a radial distance from a longitudinal axis of the introducer.

5. A method of simultaneously or substantially simultaneously obtaining tissue samples and placing fiducial markers at multiple locations within an organ or tissue, comprising:
   positioning an introducer assembly at a desired location within the organ or tissue, the introducer assembly comprising a conduit and a stylet;
   removing the stylet from the introducer assembly;
   coupling a biopsy device to the introducer assembly, the biopsy device having a plurality of tine assemblies wherein each tine assembly comprises an inner portion disposed within an outer portion;
   retracting a sliding member of the biopsy device against a biasing force of a biasing member, wherein the sliding member carries the outer portions of the tine assemblies;
   adjusting the biopsy device to a selected deployment distance by adjusting an axial position of the biopsy device relative to the conduit;
   simultaneously or substantially simultaneously deploying the inner portions of the tine assemblies the deployment distance such that distal end portions of the inner portions of the tine assemblies are distributed at spaced locations from one another, wherein the deploying of the inner portions of the tine assemblies comprises pressing a trigger of the biopsy device and wherein the inner portions are directly coupled to the trigger;

releasing the sliding member such that the biasing member moves the sliding member to deploy the outer portions of the tine assemblies to obtain the tissue samples and deploy the fiducial markers, wherein each fiducial marker has a rod shape with a plurality of notches in the radial direction of the each fiducial marker, and wherein each notch of the plurality of notches extends between 70% to 90% of a diameter of the each fiducial marker.

6. The method of claim 5, wherein the releasing of the sliding member is accomplished by further pressing of the trigger of the biopsy device.

7. The method of claim 6, wherein the releasing of the sliding member occurs after the inner portions have been deployed substantially to the deployment distance.

8. A combination biopsy and marker placement device, comprising:
- a first portion comprising an introducer conduit and a stylet;
- a second portion that is securable to the first portion at a selected relative position within a range of available positions, the second portion comprising:
- a body;
- a slider movable along a longitudinal axis of the device;
- a biasing element that biases the slider in a deployment direction;
- a trigger movable along the longitudinal axis of the device;
- a plurality of tine assemblies, wherein an inner portion of each of the tine assemblies is coupled for movement with the trigger and an outer portion of each of the tine assemblies is coupled for movement with the slider, wherein each tine assembly carries a marker;

wherein, in use, the introducer conduit is positioned at a desired location within an organ or tissue and the stylet is removed from the introducer conduit, the second portion is coupled to the first portion at the selected position, the slider is retracted against the force of the biasing element, the trigger is depressed to simultaneously or substantially simultaneously deploy the inner portions of the tine assemblies and the slider is released to deploy the outer portions of the tine assemblies, wherein tissue samples are taken when the outer portions of the tine assemblies are deployed over the inner portions, and wherein when the tine assemblies are removed the markers are left in place, wherein each marker has a rod shape with a plurality of notches in the radial direction of the each marker, and wherein each notch of the plurality of notches extends between 70% to 90% of a diameter of the each marker.

9. The device of claim 8, wherein the trigger is configured to release the slider once the inner portions of the tine assemblies are substantially deployed.

10. The device of claim 8, wherein the inner portions of the tine assemblies carry the markers and the markers are separated from the inner portions by the movement of the outer portions over the inner portions.

11. The device of claim 8, wherein a distal end of each tine assembly has a curved shape and is restrained in a generally linear orientation by the introducer conduit.

12. The device of claim 8, further comprising an adjustment mechanism to permit adjustment of the introducer conduit relative to the tine assemblies to adjust a deployment distance of the tine assemblies.

13. The device of claim 8, further comprising a retention mechanism for retaining the slider in a retracted position until released.

* * * * *